United States Patent
Martino et al.

(10) Patent No.: US 6,736,509 B2
(45) Date of Patent: May 18, 2004

(54) ABERROMETER ILLUMINATION APPARATUS AND METHOD

(75) Inventors: Ronald J. Martino, Geneva, NY (US); David F. Prelewitz, Rochester, NY (US); Kevin Kearney, Fairport, NY (US)

(73) Assignee: Bausch and Lomb, Inc., Rochester, NY (US)

( * ) Notice: Subject to any disclaimer, the term of this patent is extended or adjusted under 35 U.S.C. 154(b) by 0 days.

(21) Appl. No.: 10/027,377

(22) Filed: Dec. 21, 2001

(65) Prior Publication Data
US 2003/0117581 A1 Jun. 26, 2003

(51) Int. Cl.⁷ ................................................. A61B 3/10
(52) U.S. Cl. ..................................................... 351/221
(58) Field of Search ................................. 351/205, 206, 351/211, 212, 214, 219, 221, 246, 247; 356/124; 606/4, 5

(56) References Cited

U.S. PATENT DOCUMENTS

| | | |
|---|---|---|
| 5,777,719 A | 7/1998 | Williams et al. ............ 351/212 |
| 6,095,651 A | 8/2000 | Williams et al. ............ 351/246 |
| 6,155,684 A | 12/2000 | Bille et al. .................. 351/212 |
| 6,264,328 B1 | 7/2001 | Williams et al. ............ 351/221 |
| 6,270,221 B1 | 8/2001 | Liang ......................... 351/221 |
| 6,271,915 B1 | 8/2001 | Frey ............................ 356/124 |
| 6,460,997 B1 * | 10/2002 | Frey et al. ................... 351/205 |
| 6,598,975 B2 | 7/2003 | Liang et al. ................. 351/221 |

FOREIGN PATENT DOCUMENTS

| | | | |
|---|---|---|---|
| DE | 19926274 A1 | 1/2001 | .......... A61B/3/107 |
| DE | 10014480 A | 9/2001 | .......... A61F/9/007 |
| WO | 00/10448 | 3/2000 | .......... A61B/3/103 |

OTHER PUBLICATIONS

U.S. Pub. No. 20020007176A1 Entitled "Optimization of Ablation Correction of an Optical System and Associated Methods" by Campin, et al.

* cited by examiner

Primary Examiner—George Manuel
(74) Attorney, Agent, or Firm—Craig E. Larson

(57) ABSTRACT

A wavefront-sensing device for measuring ocular aberrations includes, among other things, a retinal illumination component and a wavefront imaging component (e.g., a microlens array for a Shack-Hartmann wavefront sensor). The retinal illumination component includes a laser source and a fixed collimating lens. In one embodiment, an improved device has a beam path between the retinal illumination component and the patient's eye containing no refracting, diffracting, or phase altering components for focusing the illumination beam on the retina. In another embodiment, the retinal illumination component provides a beam having a diameter on the retina that is smaller than the diffraction limit of the wavefront imaging component over a refractive focus range of the patient's eye of between about $-12D$ to $+6D$.

16 Claims, 4 Drawing Sheets

ABERROMETER ILLUMINATION APPARATUS AND METHOD

BACKGROUND OF THE INVENTION

1. Field of the Invention

The present invention pertains to the field of wavefront sensing and, particularly, to an improved ophthalmic aberrometer and method for retinal illumination.

2. Description of Related Art

A wavefront sensor, often referred to as an aberrometer (which terms will be used interchangeably herein), is a device that measures a difference in the optical path of light between a deformed wavefront and an ideal or reference wavefront. A properly processed measurement yields values for various aberrations in the optical system that the light propagates through. Recent attention has focused on the design and use of wavefront sensors for measuring the aberrations of the eye with the goal of improving visual quality. Williams' U.S. Pat. No. 5,777,719 describes a Shack-Hartmann type wavefront sensor that can be used to measure, among other parameters, higher-order ocular aberrations. Shack-Hartmann wavefront sensors are characterized by a microlens (lenslet) array for imagining the light reflection from the retina into an array of spots on a detector. The resulting spot image array is displaced from the regular array resulting from an unaberrated optical system. These displacements of the spots are used to determine the wavefront slope at each spot location and this information is typically used to determine the coefficients of Zernike polynomials which represent different orders and modes of the wavefront aberrations. Other types of aberrometers include the spatially resolved refractometer based on the Scheiner optometer, those based on the Tscheming principle, skiascopic systems, scanning systems of the Tracey technology type, raytracing devices, and others. All of these aberrometer types are well known in the ophthalmic wavefront sensing art so that a detailed description of these devices is not necessary to understand the invention. Descriptions of these devices can be found, for example, in *J. Refractive Surg.* 16 (5), September/October 2000.

Regardless of the sensing principles of different type aberrometers, they all require a retinal illumination source. This is typically a light emitting diode, a superluminescent diode (SLD), a diode laser (typically operated below threshold) or, another, preferably partially-coherent source that produces a point source on the patient's retina. In fact, it is highly desirable that the eye illumination focus on the eye's fovea so that the ultimate wavefront measurement represents aberrations at the fovea, the highest resolution portion of the retina. Illumination that covers an area larger than the fovea will produce less accurate aberration values. Generally, patient refractive error is the largest optical defect to contend with in aberrometer wavefront measurement. Such error limits the measurement range of the aberrometer. The typical ophthalmic patient will have an uncorrected defocus in a wide range between ±15 diopters (D). This means that the eye will focus light some distance either in front of or behind the retinal plane, producing blurry images on the retina when this value is different from zero.

Lasers (used herein throughout to refer to the retinal illumination source) used for providing the retinal illumination typically have beam diameters of about 1.5 mm. Since the fovea of the eye is also about 1.5 mm in diameter, any defocus power in the eye will inhibit a tight match between the illuminating beam and the retinal target. Aberrometers are generally constructed such that their optical systems include refocusing means to account for the patient's refractive power, and also, so that the wavefront image spots are in focus on the wavefront detector. The refocus of the laser beam can be accomplished by injecting it in a position in the aberrometer optical system so that the refocus occurs with the correction of the patient's defocus. Alternatively, a separate focussing optical path can be provided for the illumination light. These solutions require that the laser beam pass through refracting optics (lenses). The principal drawback, however, is the noise generated in the wavefront sensor from backscatter due to the inherent disparity in light intensity between the light entering and exiting the eye. For 780 nm light, for example, approximately 0.1% of the illumination light is collected for wavefront imaging. The solution provided by polarization optics is too costly to be effective.

Another concern for accurate wavefront measurement is the compensation of refractive errors on the input side of aberration measurement. One approach for providing a small illumination spot on the fovea was to create a best focus by geometrically correcting the input light by either adding or subtracting optical power from a plane wave. Hence, the input light would diverge or converge to compensate for myopia or hyperopia, respectively. In a myopic eye with a small pupil diameter, however, the input beam is diverging before intercepting the cornea, and the input light profile can take on a significant aberration signature prior to striking the retina. This can seriously degrade the intensity profile distribution which can interject error in localizing (centroiding) the imaged spot on the fovea and, in turn, in the wavefront reconstruction. Moreover, a very small input beam will suffer from diffraction effects and reduce measurement range.

Spot asymmetry on the fovea is a further concern affecting accurate wavefront measurement. Poor or inaccurate localization of imaged lenslet spots can create errors in the Zernike polynomial terms of the reconstructed wavefront. Since a Shack-Hartmann device senses a differentiated wavefront, the Zernike terms are no longer mutually independent (i.e., non-orthogonal). As such, system noise can induce Zernike term cross-coupling leading to artificially created Zernike quantities that do not actually exist.

Accordingly, the inventor has recognized a need for a retinal illumination apparatus in an aberrometer and associated method that address the disadvantages of the current technology. These and other advantages and objects of the present invention will become more apparent in view of the following description and figures.

SUMMARY OF THE INVENTION

The invention is generally directed to illuminating a patient's retina for making a wavefront measurement with an illumination beam having a beam characteristic, e.g., diameter or profile, that a) eliminates the need to refocus between the source and the patient's cornea, and b) which maintains a beam spot area on the fovea that is smaller than the diffraction limit of a wavefront imaging component over a defocus range typically encountered in the patient population; i.e., between about −12D to +10D and, preferably, between −12D (±0.25D) to +6D (±0.25D). An embodiment of the invention is directed to an improved wavefront sensing device. The improvement is characterized by the aberrometer having an optical path between a retinal illumination source and a patient's eye containing no refractive, diffractive, or other phase altering components. In other words, only beam steering components, if any, are present in the optical path between the retinal illumination source and the patient's eye. Thus, the effective use of Gaussian wave propagation will provide a tight beam waist and a Rayleigh range that extends over a specified refractive error range. Preferably, the beam diameter of the illumination beam at the patient's anterior cornea is less than 1 mm. The retinal illumination source is preferably a 780 nm diode laser assembly including an integrated collimating lens; alternatively, a SLD or other source producing coherent or semi-coherent light of a suitable wavelength, plus fixed lens component, may provide the appropriate illumination size and profile. The wavefront imaging component for imaging at least a portion of the unknown wavefront on a detector is preferably a lenslet of o microlens array of a Shack-Hartmann sensor.

In another embodiment, a method of making a more accurate wavefront measurement of a patient's eye comprises illuminating the patient's retina with an illumination beam over an optical path between the source and the patient's eye that is free of any refracting, diffracting or phase altering components. An aspect of this embodiment involves providing foveal illumination with a beam diameter that is less than a diffraction limit value of an imaging component that images a portion of the wavefront on a detector over a refractive focus range of the patient's eye between about −12D to +6D. The method further entails providing a Gaussian illumination beam having a Rayleigh range that is greater than the refractive focus range of the patient's eye between about −12D to +6D.

These and other objects of the present invention will become more readily apparent from the detailed description to follow. However, it should be understood that the detailed description and specific examples, while indicating the preferred embodiments of the invention, are given by way of illustration only, since various changes and modifications within the spirit and scope of the invention will become apparent to those skilled in the art based upon the description and drawings herein and the appended claims.

DETAILED DESCRIPTION OF PREFERRED EMBODIMENTS

Figure 1:
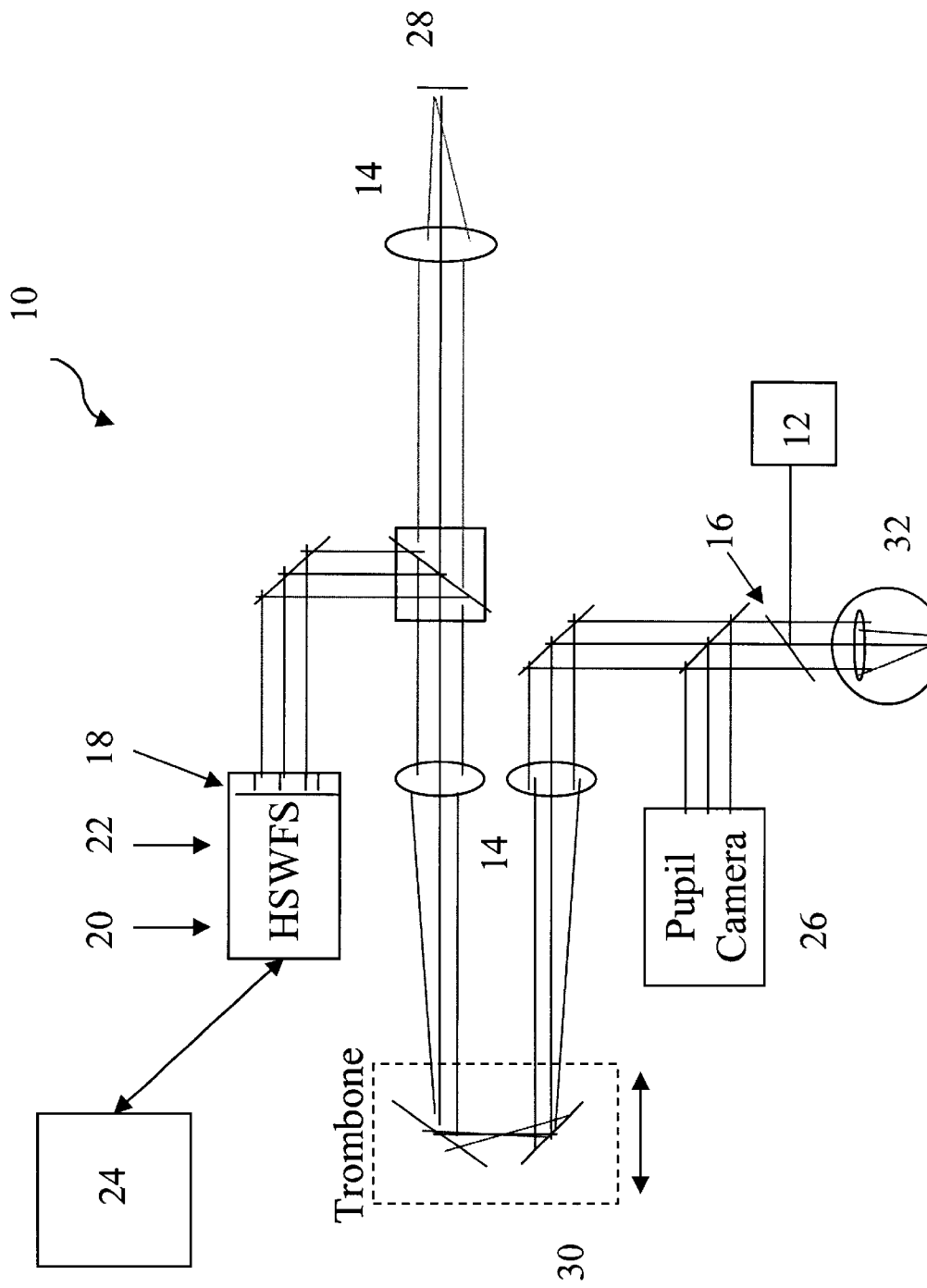
FIG. 1 is an optical schematic of a wavefront sensor according to an embodiment of the invention.

FIG. 1 is an illustration of an improved wavefront sensor in the form of a Shack-Hartmann aberrometer 10 according to an embodiment of the invention. It will be appreciated that the invention is not limited to a Shack-Hartmann aberrometer, but in fact applies to all aberrometers and wavefront sensing methods that require point source retinal illumination and wavefront imaging for aberration analysis. Generically, an aberrometer 10 requires an optical head, a data acquisition, storage and processing system for detecting, measuring and displaying wavefront aberration data, and interlinking electronics and software. The optical head encompasses an illumination component 12, preferably in the form of a 780 nm laser diode illumination source 70 that outputs a Gaussian, preferably coherent, transverse mode beam and an integrated collimating lens 72; imaging lenses 14 and beam splitters 16 for manipulating transmitted and reflected light from the illumination component 12; a microlens array 18 for imaging unknown wavefront light from the eye's retina; a CCD or CMOS sensor 20 for detecting image centroids, connected to the wavefront camera 22; a processing system 24 which includes a P.C. with appropriate software for calculating the aberration data, and a display (not shown); and alignment camera 26. A fixation target 28 aids in the alignment and measurement of the patient's eye 32. The wavefront sensing device 10 preferably includes an optical trombone system 30 (or alternative optical focusing system) to compensate for refractive error in the patient's eye. Preferably, the trombone will compensate for −15D to +10D of spherical defocus, although the range of about −12D to +6D (±0.25D) is the preferred range and what is typical of the general population.

According to an embodiment of the invention, the laser beam optical path between the laser illumination component 12 and the eye 32 contains only beamsplitter 16 for steering the beam to the eye. Noticeably absent are any refracting, diffracting, or phase altering optical components for refocusing the laser beam on the patient's retina to compensate for myopic or hyperopic refractive error, other than the collimating lens 72 that is fixedly positioned with respect to the laser diode itself for producing the beam characteristics described in greater detail below.

Figure 2:
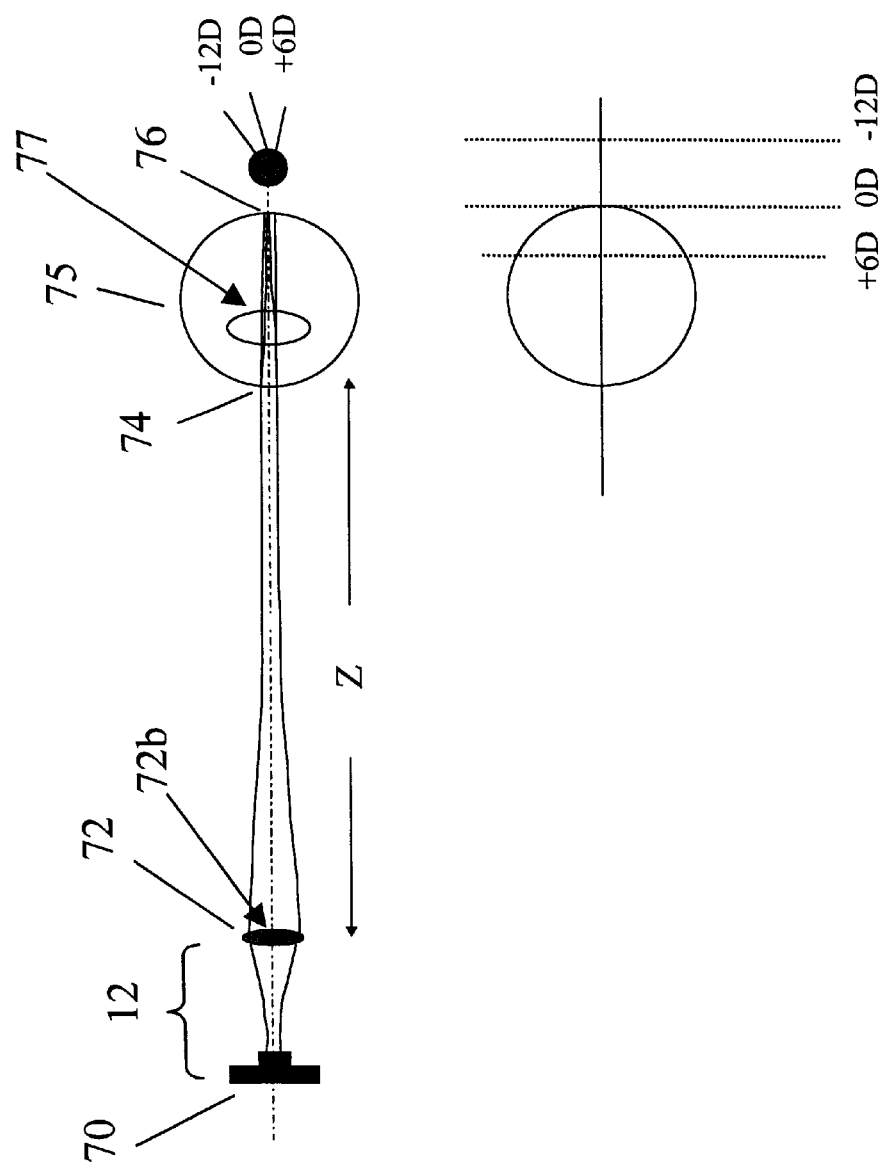
FIG. 2 is a schematic diagram showing an illumination component and output retinal illumination beam over a typical range of defocus in the eye according to an embodiment of the invention.

FIG. 2, in part, illustrates an aspect of the invention pertaining to providing an illumination beam on a patient's fovea having a beam diameter that remains less than the diffraction limit of a component that images the reflected, unknown wavefront from the retina onto a detector for wavefront image analysis over the range of −12D to +6D without external focusing. In a preferred embodiment, the wavefront sensor device is a Shack-Hartmann aberrometer. Accordingly, the imaging component is a microlens array in which the diffraction limit of an individual lenslet is known to be $2.44\lambda f/d$, where $\lambda$ is the illumination wavelength, f is the lenslet focal length and d is the lenslet diameter. In an exemplary illustration, $\lambda=785$ nm, and f=6.0 mm, d=0.2 mm making each lenslet f/30, and giving a diffraction limit value equal to $57\mu$. The illumination component 12 consists of laser diode 70 and collimating lens 72 that is fixed in position with respect to the laser 70. The laser is a 785 nm Blue Sky Research CircuLaser Diode (PS108-00) that provides a circularized beam with a total divergence of 10 degrees. The collimating lens 72 is a Geltech molded asphere 350200 that was chosen due to its short focal length and reasonable cost (available from Thorlabs already coated and mounted). The focal length is chosen so that the laser beam diameter incident on the cornea is very small, preferably 1 mm or less, to avoid effects of wavefront error of the eye on the input pass. A ZEMAX® optical raytrace eye model was created in correspondence with FIG. 2 to assess the predicted spot sizes on the cornea 74 and the retina 76. The model contains the laser source 70, the collimating lens 72, and a model (Gullstrand) of a normal eye 75. The axial distance from the second surface 72b of the collimating lens 72 to the anterior cornea 74 is 104.92 mm. The distance from the laser 70 to the collimating lens 72 is 0.735 mm. Gaussian beam propagation is used to simulate the behavior of the laser beam with a Gaussian cross sectional intensity distribution. A 2 micron input beam waist was assumed. Ray trace analysis shows the beam diameter at the cornea at roughly 0.46 mm, well within the goal of 1 mm or less. The size of the spot on the retina, 64 microns, corresponds to an angular range of +/−0.11 degrees exiting the eye. This is calculated using the geometric relationship h=F tan(θ), where h is the object height, F is the lens focal length (for the eye, this is roughly 17 mm), and θ is the field angle. The beam approaching the trombone now has an angular subtent of +/−0.11 degrees. Upon exiting the trombone, this is increased to +/−0.12 degrees due to the angular magnification of the trombone. The trombone for the specific design at hand is made up of two lenses with focal length ratio of 1.075, thus increasing the angle by that factor. The beam now exits the trombone heading toward the lenslet array with an angular spread of ±0.12 degrees. As it enters the lenslet array, each lens converts the angular subtent to an image size, using the same equation h=F tan(θ). Since the lenses each have focal length of 6 mm, they each create a spot diameter of 2 h=2×6 mm×tan(0.12 degrees)=25 microns on the detector. This is significantly smaller than the diffraction spot size for the f/30 lenslets of 57μ. Therefore, due to the trombone magnification and the lenslet focal length, we get spots imaged onto the detector which are smaller than the spot size on the retina. There are several other combinations of trombone magnification and lenslet focal length that would give the same result. For other cases, as described below, the spot size on the retina varies, but is always smaller at the image (detector behind the lenslet array).

To simulate refractive errors, the distance from the back of the eye lens 77 to the retina 76 was lengthened to simulate nearsightedness and shortened to simulate farsightedness. For the patient with the −12D refractive error, the spot size on the retina is even smaller, meaning that for this length eyeball, the retina is closer to the minimum beam waist position. For the +6D patient, the spot on the retina could be as large as 94 microns diameter. This corresponds to 37 micron spots at the wavefront sensor. The distance from the laser 70 to the collimating lens 72 can be varied to place the minimum beam waist on the retina 76 for a different case. The solution described above minimizes the spot size for the 0D case. However, as this distance is shortened, the spot for the 12D patient can get as small as 10 microns, but not without the spot for the +6 diopter patient growing to 95 microns.

It will be appreciated that stated that the magnification is an important aspect to this approach. Given that the lenslet array is an optical system, it will always magnify (or de-magnify) from object to image; in this case, the spot projected onto the retina to the camera sensor. The angular spread of the blur spot (Airy spot or the diffraction limited spot) of the lenslet must always be greater than the subtended angle of the object (the retinal spot). Thus one can choose both the laser injection optics and the wavefront camera imaging optics (the lenslet, and to a much lesser degree, the trombone optics) such that this will always be so over the whole refractive error range.

Figure 3:
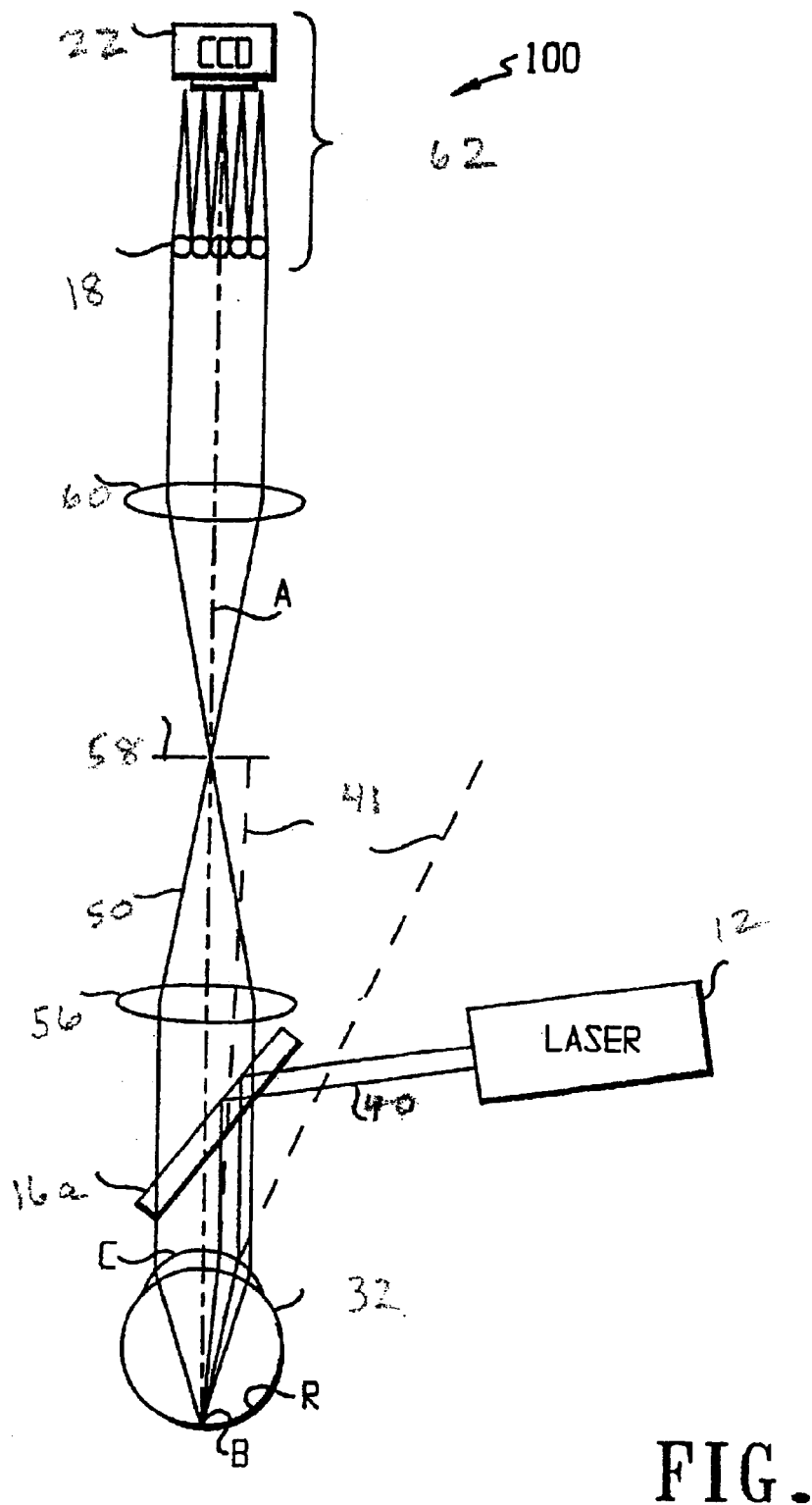
FIG. 3 is an optical schematic of an off-axis illumination system according to the invention.

It is also preferable to keep corneal back-reflections out of the wavefront-sensing path. In an aspect of this embodiment, the illumination component 12 is positioned off-axis relative to the patient's eye 32 as shown schematically in FIG. 3. FIG. 3 shows an overview of a basic Shack-Hartmann aberrometer system 100 for off-axis illumination of the retina R. The laser component 12 emits beam 40 towards beamsplitter 16a. The illumination component 12 and beamsplitter 16a are positioned such that the light beam 40 impinges the eye 32 off of the optical axis A of the eye. Thus, a light beam 41 reflected from the cornea 42 of the eye is reflected off of the optical axis A. The remaining light forms a laser beacon B on the retina R of the eye 32. The eye's optics propagate a light beam 50 out of the eye that passes through the beamsplitter 16a. Beam 50 then passes through a lens 56, a stop 58 which passes the beam 50 while blocking the beam 41 reflected from the cornea, and a lens 60 to a Hartmann-Shack detector 62. The detector 62 comprises the lenslet array 18 to focus the beam 50 as an array of light spots onto a CCD or other suitable two-dimensional detector 22. The beam 40 will exhibit the Gaussian characteristics described above for maintaining a retinal spot diameter that remains less than the diffraction limited spot size from the lenslets of the array 18.

Figure 4:
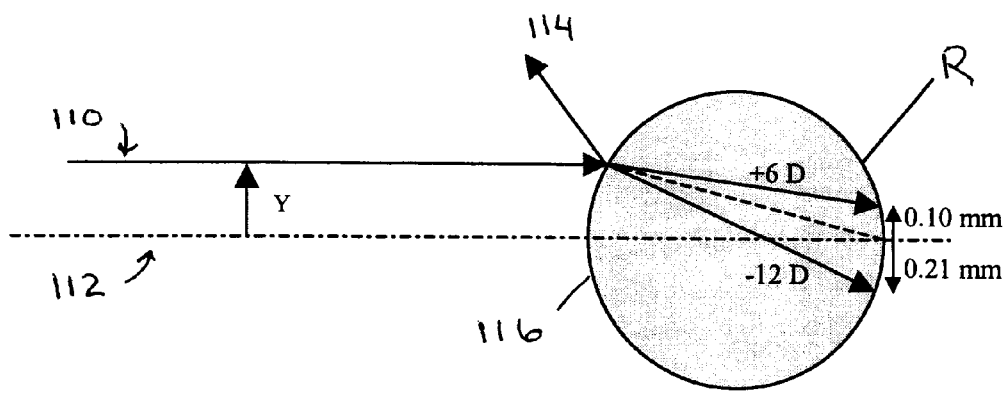
FIG. 4 is an optical schematic of an off-axis illumination system according to another embodiment of the invention.

In an alternative aspect illustrated with reference to FIG. 4, the collimated laser beam 110 is offset laterally from the eye optical axis 112 to direct corneal back reflections 114 out of the wavefront-sensing path. Based on the typical radius of the anterior cornea surface 116, an offset, Y, of between about 0.5 mm to 1 mm is suitable with a preferable offset being between about 0.7 mm to 1 mm. It is also preferable that the lateral offset, Y, be in the vertical direction (up or down in FIG. 4) due to the fact that the lateral position of the corneal vertex with respect to the geometric center of the pupil will vary from patient to patient. These differences can vary from 0.1 mm up to 0.6 mm; however, this difference is usually smaller in the vertical direction. Due to the lateral offset of the incoming beam, the position of the spot on the retina, R, will vary as a function of refractive error. As shown in FIG. 4, for a 1 mm offset the variation could be up to 0.1 mm for far-sighted patients, and 0.21 mm for the most near-sighted patient. Angularly, these correspond to 0.34 degrees, and 0.7 degrees, respectively. Therefore, for patients with −4.7 to +4.0 diopters, the spot will be within the foveola (0.5 degree diameter), and all cases will be well within the fovea (5 degree diameter). The presence of corneal back reflections at the detector can be detected and the operator can be alerted, accordingly, to make adjustment. This can be done by moving the laser in the instrument, or the entire instrument relative to the patient if it can be moved in sub-millimeter increments. As long as this difference is recorded, it should not upset the mapping of the measured wavefront to the patient's eye.

A method embodiment according to the invention is directed to obtaining a more accurate ocular wavefront aberration measurement with a wavefront-sensing device. In one aspect, a retinal illumination source is provided having beam characteristics that eliminate any need to refocus the beam along a propagation path between the illumination source and a patient's eye. The preferable beam characteristics are a Gaussian profile with a beam waist that is effectively of constant diameter over the refractive range of the eye, preferably over a refractive range between about +6D to −12D. In a related aspect, it is preferable to provide a retinal illumination beam having a diameter on the eye's retina that is less than a diffraction limit value of an imaging component used to image a portion of the wavefront on a detector over a refractive focus range of the patient's eye between about −12D to +6D.

While various advantageous embodiments have been chosen to illustrate the invention, it will be understood by those skilled in the art that changes and modifications can be made therein without departing from the scope of the invention as defined in the appended claims.

We claim:

1. An improved wavefront sensing device for measuring an aberrated wavefront from a patient's eye, said device comprising an optical head including a retinal illumination component, a data acquisition, storage and processing system including a lenslet array for imaging the aberrated wavefront on a detector, and interlinking electronics integrated to detect, measure and display ocular aberration information, the improvement characterized by:

the retinal illumination component providing a collimated beam having a Gaussian beam characteristic, along an optical path in the device intermediate the illumination component and the patient's eye having no refractive, diffractive or phase altering components.

2. The device of claim 1, wherein the illumination component comprises a light source and a collimating lens that is fixedly positioned with respect to the light source.

3. The device of claim 2, wherein the light source comprises one of a diode laser, a laser diode, and a super luminescent diode.

4. The device of claim 2, wherein the light source emits a wavelength in the range of about 780 nm to 800 nm.

5. The device of claim 1, wherein the beam has a diameter on the retina that is less than a diffraction limit value of the lenslet forming a spot image of a portion of the aberrated wavefront on the detector over a refractive power range of the eye between about −12D to +6D.

6. The device of claim 1, wherein the beam has a Rayleigh range that is equal to or greater than a refractive power range of the eye between about −12D to +6D.

7. The device of claim 1, wherein the optical path is displaced from an optical measurement axis of the device.

8. The device of claim 7, wherein the displacement is a parallel translation of between about 0.6 mm to 1.0 mm measured at the posterior corneal surface.

9. The device of claim 1, wherein the retinal illumination component is positioned relative to the patient's eye such that light reflected from a corneal surface of the eye travels along a first path and such that light reflected from the retina travels along a second path that is spatially separated from the first path.

10. The device of claim 1, wherein the collimated beam has a diameter, d, at an anterior corneal surface, where $d<1$ mm.

11. The device of claim 10, wherein $0.46\ mm<d<1\ mm$.

12. An ophthalmic wavefront sensing device comprising a retinal illumination component that provides a beam to a foveal surface of a patient's eye having a characteristic beam diameter that is less than a diffraction limit value of a wavefront imaging component over a refractive range of the patient's eye between about −12D to +6D.

13. The device of claim 12, wherein the beam is a Gaussian beam.

14. The device of claim 12, wherein the device is a Shack-Hartmann wavefront sensor.

15. A method for obtaining a wavefront measurement of a patient's eye with an aberrometer, comprising the steps of:

providing a retinal illumination beam having a diameter on the eye's retina that is less than a diffraction limit value of a lens used to image a portion of the wavefront on a detector over a refractive focus range of the patient's eye between about −12D to +6D.

16. The method of claim 15, comprising providing a Gaussian illumination beam having a Rayleigh range that is greater than the refractive focus range of the patient's eye between about −12D to +6D.

* * * * *